US010501851B2

(12) United States Patent
Kianinia et al.

(10) Patent No.: US 10,501,851 B2
(45) Date of Patent: Dec. 10, 2019

(54) ATTACHMENT OF NANO-OBJECTS TO BEAM-DEPOSITED STRUCTURES

(71) Applicant: FEI Company, Hillsboro, OR (US)

(72) Inventors: Mehran Kianinia, Ashfield (AU); Olga Shimoni, Wahroonga (AU); Igor Aharonovich, Waterloo (AU); Charlene Lobo, Redfern (AU); Milos Toth, Redfern (AU); Steven Randolph, Portland, OR (US); Clive D. Chandler, Portland, OR (US)

(73) Assignee: FEI Company, Hillsboro, OR (US)

( * ) Notice: Subject to any disclaimer, the term of this patent is extended or adjusted under 35 U.S.C. 154(b) by 431 days.

(21) Appl. No.: 15/188,862

(22) Filed: Jun. 21, 2016

(65) Prior Publication Data

US 2017/0327951 A1     Nov. 16, 2017

Related U.S. Application Data

(60) Provisional application No. 62/335,423, filed on May 12, 2016.

(51) Int. Cl.
| C23C 16/48 | (2006.01) |
| C23C 16/56 | (2006.01) |
| H01J 37/317 | (2006.01) |
| B82Y 40/00 | (2011.01) |
| G01N 33/543 | (2006.01) |

(52) U.S. Cl.
CPC .......... *C23C 16/487* (2013.01); *C23C 16/56* (2013.01); *H01J 37/317* (2013.01); *B82Y 40/00* (2013.01); *G01N 33/54353* (2013.01); *H01J 2237/31732* (2013.01)

(58) Field of Classification Search
CPC ................................................ G01N 33/54353
See application file for complete search history.

(56) References Cited

U.S. PATENT DOCUMENTS

| 7,612,424 B1 | 11/2009 | Espinosa et al. |
| 2008/0038830 A1 | 2/2008 | Ure et al. |
| 2011/0070381 A1 | 3/2011 | Toth et al. |
| 2012/0193530 A1 | 8/2012 | Parker et al. |
| 2012/0196440 A1 | 8/2012 | Botman et al. |
| 2014/0065319 A1 | 3/2014 | Randolph et al. |

(Continued)

FOREIGN PATENT DOCUMENTS

| EP | 2570519 A2 | 3/2013 |
| EP | 2814050 A2 | 12/2014 |
| WO | 2009088779 A2 | 7/2009 |

OTHER PUBLICATIONS

Abramson, J., et al. "Quantum dot nanoarrays: self-assembly with single-particle control and resolution", Advanced Materials, Mar. 19, 2012, pp. 2207-2211, vol. 24, Issue 16, WILEY-VCH Verlag GmbH & Co. KGaA, Weinheim.

(Continued)

*Primary Examiner* — Joel G Horning (57) ABSTRACT

Beam-induced deposition decomposes a precursor at precise positions on a surface. The surface is processed to provide linker groups on the surface of the deposit, and the sample is processed to attach nano-objects to the linker groups. The nano-objects are used in a variety of application. When a charged particle beam is used to decompose the precursor, the charged particle beam can be used to form an image of the surface with the nano-objects attached.

20 Claims, 6 Drawing Sheets

(56) References Cited

U.S. PATENT DOCUMENTS

2016/0032281 A1  2/2016 Utlaut et al.

OTHER PUBLICATIONS

Curto, A.G., et al. "Unidirectional Emission of a Quantum Dot Coupled to a Nanoantenna", Science, Aug. 20, 2010, pp. 930-933, vol. 329 Issue 5994, 2010, American Association for the Advancement of Science.
Dimilla, P.A., et al, "Wetting and Protein Adsorption of Self-Assembled Monolayers of Alkanethiolates Supported on Transparent Films of Gold", Journal of the American Chemical Society, Mar. 1, 1994, pp. 2225-2226, vol. 116, American Chemical Society.
Dong, S., et al. "Self-assembled monolayers of thiols on gold electrodes for bioelectrochemistry and biosensors", Bioelectrochemistry and Bioenergetics, 1997, pp. 7-13, vol. 42, Issue 1, 1997 Elsevier Science S.A.
Frimmer, M., et al. "Scanning Emitter Lifetime Imaging Microscopy for Spontaneous Emission Control", Physical Review Letters, Sep. 16, 2011, pp. 123602.1-123602.5, vol. 107, Iss. 12, 2011 American Physical Society.
Kanno, S., et al. "Assembling of engineered IgG-binding protein on gold surface for highly oriented antibody immobilization", Journal of Biotechnology, Jan. 21, 2000, pp. 207-214, vol. 76, Issues 2-3, 2000 Elsevier Science B.V.
Kim, H., et al. "Selective immobilization of proteins on gold dot arrays and characterization using chemical force microscopy", Journal of Colloid and Interface Science, Jun. 15, 2009, pp. 161-166, vol. 334, issue 2, 2009 Elsevier Inc.
Liao, H., et al. "Gold Nanorod Bioconjugates", Aug. 5, 2005, pp. 4636-4641, vol. 17 Issue 18, 2005 American Chemical Society.
Marie, R. et al. "Adsorption kinetics and mechanical properties of thiol-modified DNA-oligos on gold investigated by microcantilever sensors", Ultramicroscopy, May 2002, pp. 29-36, vol. 91, Issues 1-4, 2002 Elsevier Science B.V.
Pallandre, A., et al. "Tuning the Orientation of an Antigen by Adsorption onto Nanostriped Templates" Journal of the American Chemical Society, Mar. 8, 2005, pp. 4320-4325, vol. 127, No. 12, 2005 American Chemical Society.
Schietinger, S., et al. "Plasmon-Enhanced Single Photon Emission from a Nanoassembled Metal-Diamond Hybrid Structure at Room Temperature", Nano Letters, Mar. 20, 2009, pp. 1694-1698, vol. 9, No. 4, 2009 American Chemical Society.
Slingenbergh, W., et al. "Selective Functionalization of Tailored Nanostructures", ACS Nano, Sep. 20, 2012, pp. 9214-9220, vol. 6 No. 10, 2012 American Chemical Society.
Staude, I., et al. "Selective placement of quantum dots on nanoscale areas of metal free substrates", Phys. Status Solidi Rapid Research Letters, Jun. 5, 2014, pp. 710-713, vol. 8, issue 8, 2014 Wiley-VCH Verlag GmbH &Co. KGaA, Weinheim.
Su, T.J., et al. "The Effect of Solution pH on the Structure of Lysozyme Layers Adsorbed at the Silica-Water Interface Studied by Neutron Reflection", Langmuir, Jan. 1, 1998, pp. 438-445, vol. 14, No. 2, 1998 American Chemical Society.
Ulman, A., "Formation and Structure of Self-Assembled Monolayers", Chemical Reviews, Jun. 20, 1996, pp. 1533-1554, vol. 96, No. 4, 1996 American Chemical Society.
Urena, E., et al, "Excitation enhancement of a quantum dot coupled to a piasmonic antenna", Advanced Optical Materials, Oct. 2, 2012, pp. 314-320, vol. 24, Issue 44, 2012 WILEY-VCH Verlag GmbH & Co. KGaA, Weinheim.
Wang, L., et al. "Self-assembly of gold nanoparticles for the voltammetric sensing of epinephrine", Electrochemistry Communications, Jun. 2006, pp. 1035-1040, vol. 8, Issue 6, 2006 Elsevier B.V.
Wolters, J., et al. "Enhancement of the zero phonon line emission from a single nitrogen vacancy center in a nanodiamond via coupling to a photonic crystal cavity", Applied Physics Letters, Oct. 6, 2010, pp 141108.1-141108.3, vol. 97, Issue 14, 2010 American Institute of Physics.
Yang, M., et al. "Bioreactive Surfaces Prepared via the Self-Assembly of Dendron Thiols and Subsequent Dendrimer Bridging Reactions", Langmuir, Jan. 26, 2005, pp. 1858-1865, vol. 21, No. 5, 2005 American Chemical Society.
Zhang, S., et al. "Biological surface engineering: a simple system for cell pattern formation", Biomaterials, Jul. 20, 1999, pp. 1213-1220, vol. 20, Issue 13, 1999 Elsevier Science Ltd.
Zheng, M., et al. "Nanopatcles Comprising a Mixed Monolayer for Specific Bindings with Biomolecules", Journal of the American Chemical Society, Sep. 2, 2004, pp. 12047-12054, vol. 126, No. 38, 2004 American Chemical Society.
Lobo, Charlene, J., et al., "High Resolution Radially Symmetric Nanostructures From Simultaneous Electron Beam Induced Etching and Deposition," Nanotechnology, 2008. 6 pages, vol. 19.

ATTACHMENT OF NANO-OBJECTS TO BEAM-DEPOSITED STRUCTURES

This application claims priority from U.S. Provisional Application 62/335,423, filed May 12, 2016, which is hereby incorporated by reference.

TECHNICAL FIELD OF THE INVENTION

The present invention relates to the attachment of nano-objects to a surface, and in particular to creating attachment positions using beam-induced deposition.

BACKGROUND OF THE INVENTION

Assembling nano-objects into macroscopic arrays is required for many applications including biomaterial sensing, photonics, plasmonics and quantum information processing. Several top down assembly methods, including lithography or dip-pen techniques, as well as bottom up methods using patterned self-assembled monolayers or electrostatic self-assembly have been developed. While these methods are capable of high resolution patterning of nano-object arrays, the assembled components are only weakly bonded to the substrate and therefore cannot undergo further processing, such as wet chemistry processing steps (e.g., sonication) or subsequent lithography. Such further processing is often required for device applications where the nano-objects act as active components in microfluidic devices, as sensing probes or photon sources in which they are coupled to plasmonic structures or other optical elements.

Nano-objects are useful for sensing of bio-molecules by selective adsorption of bio-molecules to functionalized surfaces. Gold is typically chosen as a substrate for biosensing due to its inertness relative to biological systems and its ability to form sulfhydryl- or thiol-terminated surfaces (—SH). These thiol groups may spontaneously form disulfide bonds with other thiol-terminated molecules. Historically, these thiol-terminated biofunctional surfaces have been created by functionalizing a gold surface with thiol groups, followed by the introduction of alkylthiolates (R—SH) which order spontaneously and form a self-assembled monolayer, with the terminal end opposite the thiol functionalized with a biologically selective group, such as an enzyme or bio-substrate. An analyte can then be added, which selectively binds to the functionalized monolayer.

Self-assembled monolayers have been preferred due to the potential for the bulk substrate surface to impact the structure of the bio-molecule of interest. For example, proteins can be irreversibly denatured by interaction with hydrophobic or hydrophilic functionalized surfaces if such a monolayer is not used. Therefore, if the secondary, tertiary, or quaternary structure is of importance, immobilization directly on a surface is inadvisable.

The gold required for the introduction of thiol groups is typically applied using lithographic techniques, which are time consuming and expensive. A method for immobilization of bio-molecules on a surface without the intervening steps of gold application and self-assembled monolayer formation is desired.

In general, a robust, accurate method of attachment of nano-objects to a surface at precise locations is desired.

SUMMARY OF THE INVENTION

An object of the invention is to provide a system to attach nano-objects to a surface at precise locations.

Beam-induced deposition decomposes a precursor at precise positions on a surface. The sample is processed to provide linker groups on the surface of the deposit, and the sample is processed to attach nano-objects to the linker groups.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

Embodiments of the invention provide a method and apparatus for precise, selective attachment of nano-objects to specific areas on a substrate.

Attachment of nano-objects to the substrate surface is accomplished by depositing a material on the substrate using beam-induced deposition, modifying the surface properties of the deposit, and then attaching nano-objects to the modified deposit surface. This method provides selectivity in that the nano-objects attach only to the modified surface of the deposits, and not on the substrate where no deposit has been made. Nano-objects typically have a critical dimension in the range of 1 nm to 1000 nm. A critical dimension may be, for example, the diameter of a nano dot, crystal, wire, tube, sheet or flake. The attached nano-object may be an individual nano-object or a cluster comprised of multiple nano-objects, such as multiple nano-dots, nano-crystals, nanowires, or flakes.

Figure 1:
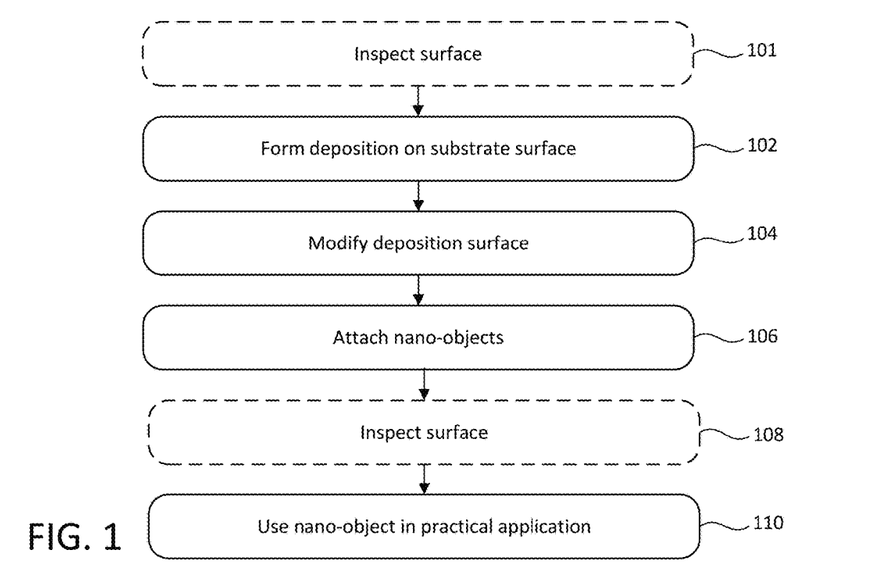
FIG. 1 is a flowchart showing a method for nano-object attachment.
Figure 2A:
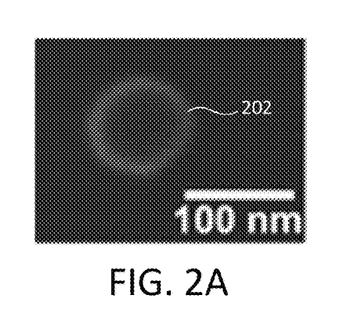
FIG. 2A is a photomicrograph showing a top-down view of a deposit.
Figure 2B:
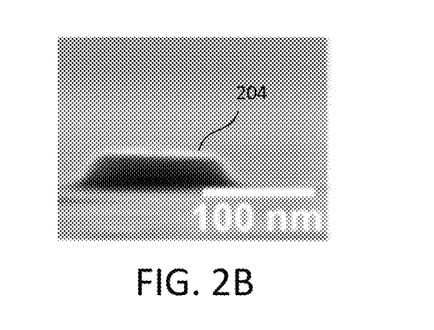
FIG. 2B is a photomicrograph showing a side view of a deposit.

FIG. 1 is a flowchart showing a method of attaching nano-objects to a substrate. In optional step 101, the surface is inspected, preferably with charged particle beam imaging. In step 102, a deposition is formed on the surface of the substrate by beam-induced deposition. Various materials can be deposited, with the use of suitable deposition precursors which are well known. FIGS. 2A and 2B show a top-down and side view, respectively, of such a deposition formed using electron-beam-induced deposition. In step 104, the surface chemistry of the deposit is modified, typically using a functionalization precursor. Preferably, the functionalization precursor affects only the beam-induced deposit, so that the entire substrate can be exposed to the functionalization precursor, and only the beam-induced deposit will be modified.

In step 106, one or more nano-objects are attached to the modified deposition surface. Because the nano-objects only adhere to the modified surface chemistry of the deposited material, the entire substrate may be exposed to the nano-objects, for example, by dipping the substrate into a bath or exposing the substrate to a gas, and the nano-objects will attach only on the beam-induced deposits. Thus, the precision of the positioning of the nano-objects on the substrate is determined by the precision of the beam-induced deposition, and the functionalization and nano-object attachment processes can be applied to the entire work piece. Attaching nano-objects can optionally be a multi-step process, with a first nano-object subsequently capturing a second nano-object. In some embodiments, the functionalized deposition is able to form covalent bonds with the nano-objects. Attachment of nano-objects by covalent bonding provides robust attachment, stronger than that provided by electrostatic interaction or physical immobilization. Covalent bonds may include, for example, disulfide bonds, sulfonamide bonds, and/or phosphonamide bonds, but the invention is not limited to these bonds.

Figure 3:
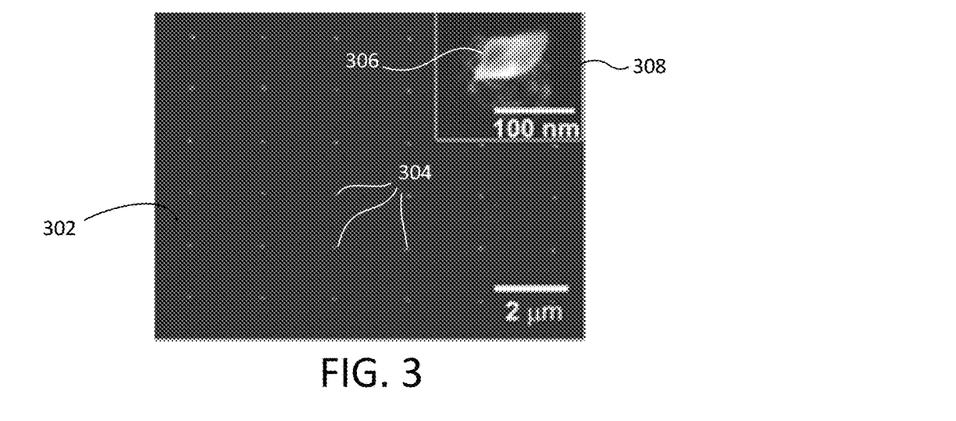
FIG. 3 is a photomicrograph showing a pattern of deposits, and the inset shows a single deposit with an attached nano-object.

In optional step 108, an image is formed of the surface having the nano-objects. For example, if beam-induced deposition is performed using a charged particle beam, a charged particle beam image, such as produced in scanning electron beam (SEM) imaging or ion-beam imaging, can be used. FIG. 3 shows an SEM image of a substrate surface 302, with a pattern of deposits 304. The inset 308 shows a magnified view of a single deposit 304, with an attached nano-object 306. In the example of FIGS. 2A, 2B, and 3, the deposit is carbon, and the attached nano-objects are nano-diamonds. It is noted no nanodiamonds are attached on the substrate surface where no deposit has been formed, displaying selective attachment of nanodiamonds to the modified deposits. In step 110, the work piece with the nano-objects attached are applied to a useful result, such as sensing biomolecules or functioning as information processing elements.

Figure 4:
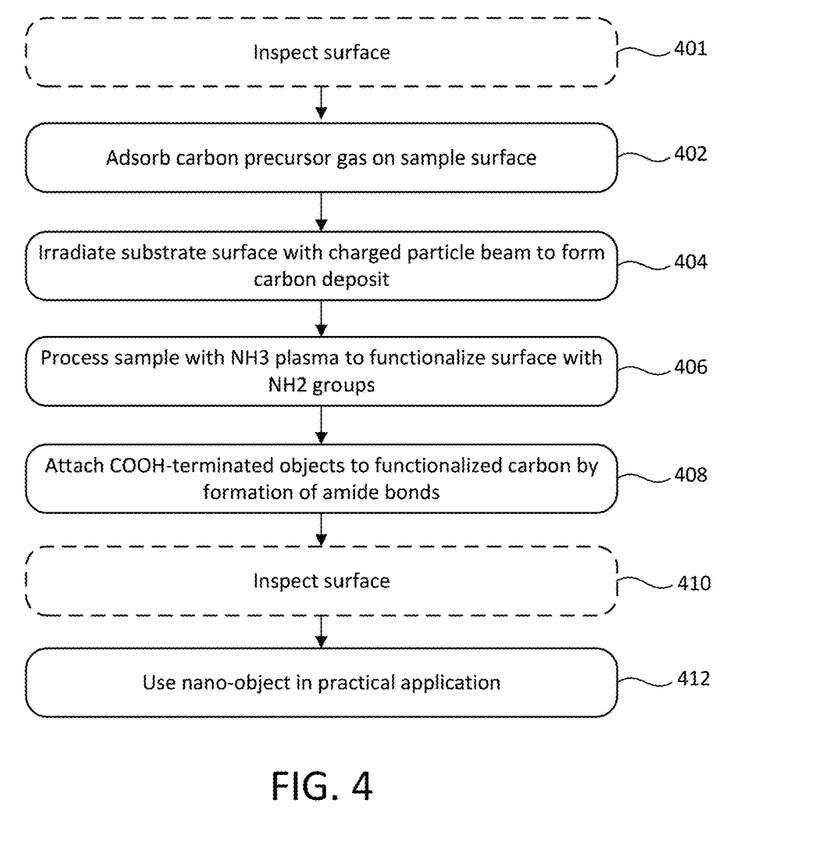
FIG. 4 is a flowchart showing a method of nano-object attachment.

FIG. 4 is a flow chart for a method of attaching nano-objects to carbon deposited by beam-induced deposition onto a substrate. In optional step 401, the surface is inspected in a vacuum chamber by charged particle beam imaging. In step 402, a carbon-bearing precursor gas is introduced into a vacuum chamber and is adsorbed onto the substrate surface. Many different carbon-bearing precursor gases, such as naphthalene, ethylene, or styrene vapor, can be used to deposit carbon. In step 404, the substrate surface is irradiated with a charged particle beam to decompose the precursor gas to form a solid carbon deposit on the surface of the substrate. Typically, this deposition process results in amorphous carbon being deposited, however deposition of other forms of carbon are possible as well. Because of the precise nature of charged particle beam processing, intricate nano-sized deposits can be accurately formed using this method. This procedure is preferably carried out within the vacuum chamber of a charged particle beam apparatus. The charged particle beam is typically an electron beam, but an ion beam or a cluster beam could also be used. A laser beam could also be used to decompose the precursor.

In step 406, the substrate surface with the deposited material is exposed to a plasma containing ammonia ($NH_3$). The $NH_3$ plasma modifies the surface chemistry of the carbon-containing deposit, resulting in the formation of amine groups (—$NH_2$) and/or amide groups (—$CONH_2$) on the surface of the carbon deposit. This substrate may be processed in the same charged particle apparatus in which the deposit was formed, or the substrate may be removed and undergo plasma processing within a different apparatus.

Following surface modification, the nano-objects are attached to the modified deposit surface in step 408. For example, nano-diamonds with terminating carboxylic acid groups (—COOH) may be bonded to the modified deposit surface by coupling with a coupling reagent, such as EDC (1-ethyl-3-(dimethylaminopropyl)carbodiimide). Such coupling covalently bonds the nano-diamonds to the modified deposit through the formation of amide bonds.

Because the —$NH_2$ groups required for amide bond formation with —COOH bearing nanodiamonds are only present on the surface of the modified deposits, nano-diamond attachment will only occur on such surfaces. This property allows the entire sample substrate to be exposed to the nano-objects, rather than localizing the application of nano-objects. For example, a sample substrate may be immersed in a solution containing EDC and nanodiamonds, with attachment only occurring on sites where amine-terminated deposits are located.

In addition, deposition within the vacuum chamber of a charged particle apparatus allows charged particle beam imaging concurrent with the deposition process. Charged particle beam imaging is performed by scanning a charged particle beam while detecting secondary or backscattered electrons, the brightness of each point on the image being determined by the number of secondary particles detected. This allows careful control of the location of deposits, and also allows metrology to be performed during deposition. In optional step 410, the electron beam is scanned across the surface and an SEM image is formed of the surface with the nano-objects attached. An SEM image can be formed during any part of the process.

Attachment of nano-objects by covalent bonding provides robust attachment, stronger than that provided by electrostatic interaction or physical immobilization. Indeed, after ultra-sonication for 12 hours, 90% of attached nanodiamonds remained affixed to a substrate surface, indicating strong attachment.

While the method of FIG. 4 functionalizes the surface with amine groups, other chemical functionalization is also possible through the use of different functionalization precursors. For example, various precursors can be used to create surfaces functionalized with —OH, —C=O, —COOH, —NO2, —SO2, —PO3, halides, —SH, or —C=S terminations can be created. An optional multi-step attachment approach may also be used. For example, functionalizing a surface may be followed by attachment of protein specific antibodies to the functionalized surface, which bind to target proteins, immobilizing them at the desired sites on the substrate.

In step 412, the nano-objects are used in a practical application. For example, a sensor can be created by attaching a dye or other chromophore to the surface of the deposit, with the presence of target molecules eliciting a color change. Alternatively, molecule-specific sensors can be created by forming the deposit on a pair of electrodes and creating a conductive surface via functionalization with polar groups. As a target molecule interacts with the surface, the conductivity between the conductors will change and may be read out as a signal.

By forming functionalized deposits of a first surface chemistry, then creating new functionalized deposits with different surface chemistry, a single substrate may have multiple functionalizations applied, for example in different areas of a TEM grid, or in the creation of assays.

Similarly, a single functionalization may be applied repeatedly, for example creating a series of first deposits and binding of a first protein-specific antibody to all available sites, followed by creation of second deposits, and binding of a second protein-specific antibody to all available sites. In such a case, the same deposition and functionalization chemistry may be used repeatedly, as the only available sites at each step are those not occupied in previous steps, allowing localization of desired binding sites for various different target molecules. Alternatively, different depositions and/or functionalization can be used sequentially.

Figure 5:
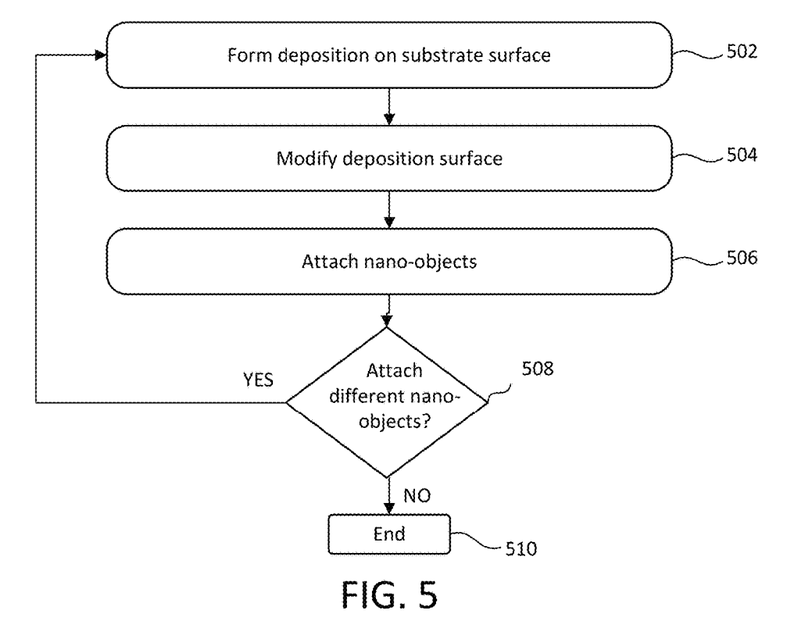
FIG. 5 is a flowchart showing a method of attaching multiple types of nano-objects attachment.
Figure 6:
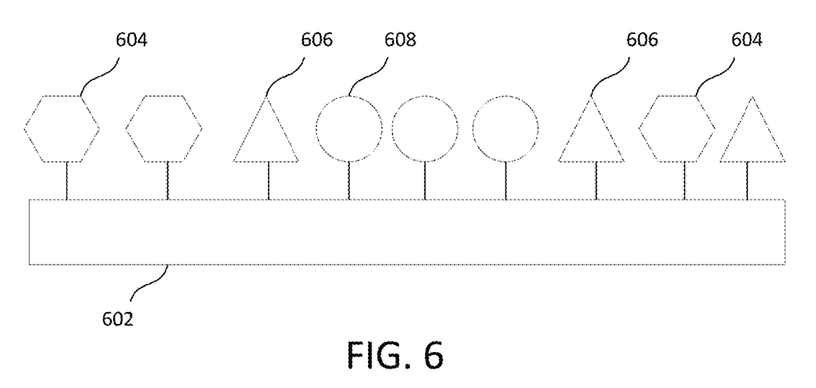
FIG. 6 shows a surface with multiple types of nano-objects attached.

FIG. 5 is a flowchart for a repeated deposition and attachment process. In step 502, a deposition is formed on the surface of the substrate. In step 504, the surface chemistry of the deposition is modified. Next, one or more nano-objects are attached to the modified deposition surface in step 506. At step 508, the decision is made if additional nano-objects, different than those attached in step 506, are to be attached. If different nano-objects are to be attached, the method returns to step 502. If not, the method ends at block 510. Either the composition of the deposition or the modification of the deposition surface may be the same as applied in earlier steps, or different, depending on the nano-objects to be attached in the current cycle. FIG. 6 shows a substrate 602 with multiple different nano-objects 604, 606, and 608 attached to the surface through subsequent deposition cycles.

The deposition, functionalization, and attachment steps may be applied towards bio-molecular analysis. In such an embodiment, the attached nano-objects are bio-molecules, such as proteins or antibodies. Charged particle deposition provides the ability to form high-aspect ratio structures, including those with a sulfurous composition. Direct deposition of such a structure allows attachment of fragile bio-molecules to the end of the structure, avoiding interaction between the bio-molecule and the underlying substrate while also avoiding the intermediary steps of gold lithography and subsequent monolayer formation used in the prior art.

Figure 7:
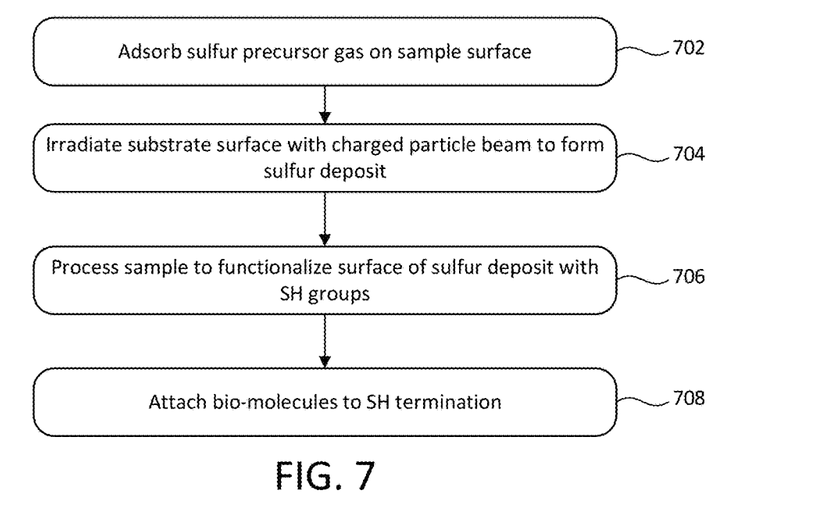
FIG. 7 is a flowchart showing another method of nano-object attachment.

Referring to FIG. 7, a method for deposition of a sulfurous deposit and subsequent functionalization and attachment of bio-molecules is shown. In step 702, a sulfur-bearing precursor gas is adsorbed on the surface of the sample substrate. The sample substrate is then irradiated with a charged particle beam in step 704, resulting in the decomposition of the sulfur-bearing precursor and the formation of a sulfurous deposit.

Several precursor chemistries offer potential for sulfur deposition, such as sulfur hexafluoride, methanesulfonamide, methanethiol, methyl disulfide, and methyl methanethiosulfonate. Other suitable sulfur-bearing precursors are known and available.

While FIG. 4 describe the deposition of a carbon-containing material and FIG. 7 describes the deposition of a sulfur-containing material, other materials can be used. For example, phosphorous may be deposited by a phosphorous-bearing precursor, such as tetrakis-trifluorophosphine platinum. While the material deposited by decomposition of tetrakis-trifluorophosphine platinum includes platinum, it also contains a large amount of phosphorus. The choice of functionalization may be different or the same for deposits having differing compositions. The application of $NH_3$ plasma gives amine and amide bonds on the surface of deposited carbon. On the surface of sulfur, sulfonamide bonds ($-SO_2-NH_2$) may be created, and on the surface of phosphorus, phosphonamide bonds ($-PO-NH_2$) may be created. Nanodiamonds, nanoparticles, biomolecules, quantum dots, and other nano-objects could be attached to the phosphorus-containing deposition.

In step 706, the sample is processed to functionalize the surface of the deposit, creating thiol terminations. The sample processing may also take place concurrently with the creation of the sulfurous deposit, combining steps 704 and 706. This can be accomplished by co-deposition with ammonia, or post-deposition processing with ammonia, thermally-cracked hydrogen, or other suitable reducing agents.

After processing to convert surface sulfur to thiol groups, bio-molecules can now be attached in step 708 to the sulfurous structure, for example by the formation of disulfide bonds between —SH containing amino acid residues in an enzyme. Further, it is commonplace to engineer bio-molecules so that one of these residues is located at a desired site along the bio-molecule, so that binding occurs at an artificially designed site within the bio-molecule.

Use of directly deposited sulfurous nano-structures circumvents the time consuming steps of gold lithography, allowing direct attachment of bio-molecules to a substrate. In addition, direct deposition process can be performed on a variety of materials on which traditional gold lithography methods are not possible or impractical.

Figure 8:
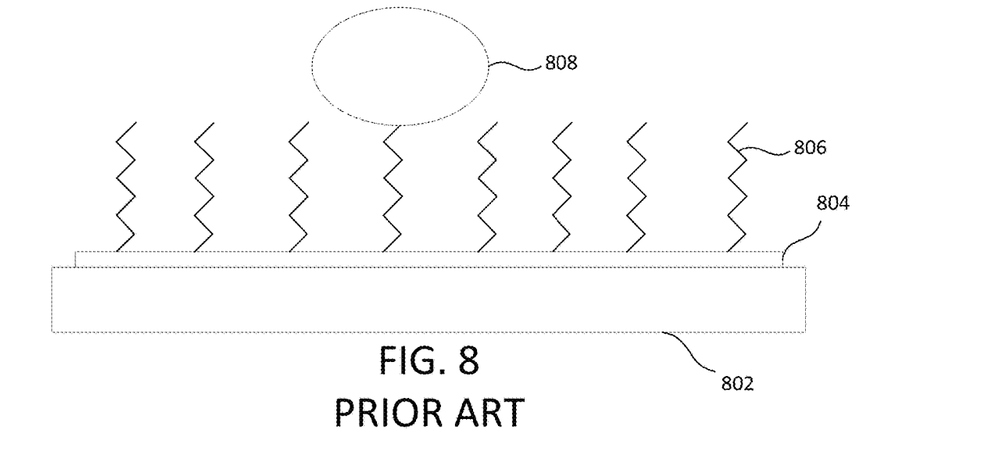
FIG. 8 shows a prior art method of attachment of nano-objects.

FIG. 8 shows a prior art method of attachment of a bio-molecule 808 to a substrate 802. A gold layer 804 is first applied by lithography, followed by the creation of a self-assembled monolayer 806. The bio-molecule 808 is then attached to the terminal end of the monolayer molecules. The bio-molecule is separated from the substrate by the monolayer, and therefore does not interact with the substrate.

Figure 9:
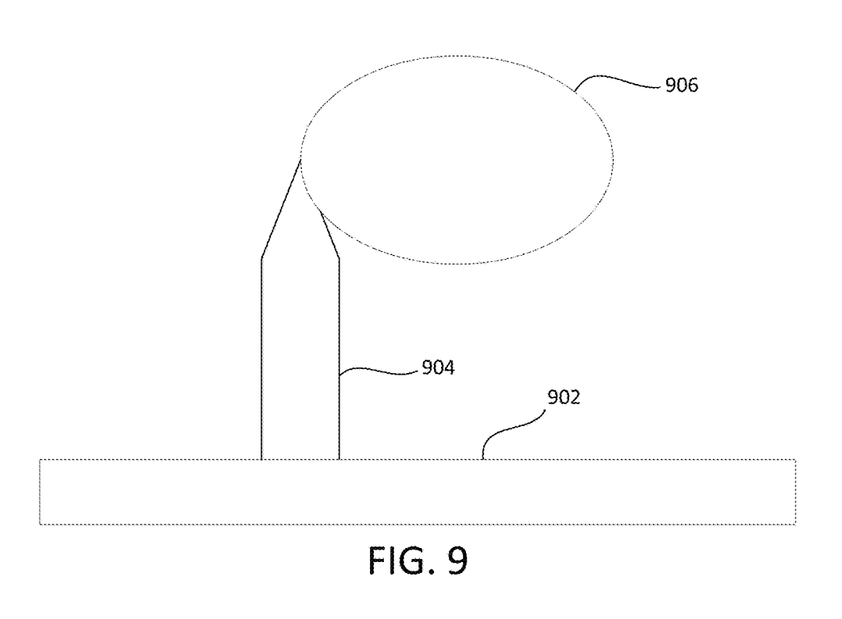
FIG. 9 shows a nano-object attached to a substrate.

FIG. 9 shows a bio-molecule 906 bonded to the end of a sulfur nanopillar 904. The nanopillar extends from the surface of the substrate 902. Similar to the prior art method of FIG. 8, the bio-molecule is separated from the substrate and does not undergo interaction with the substrate.

Indirect attachment of bio-molecules to the sulfurous structure may also be performed. For example, an enzyme may be immobilized on the end of the structure, allowing binding of other molecules while keeping them far enough away from the surface so as not to disrupt secondary, tertiary, or quaternary structure.

While much of the above discussion is directed towards thiol- or sulfhydryl-termination of a sulfurous structure, the skilled artist will recognize that other materials and termination functionalities are applicable to the attachment of bio-molecules to a substrate surface. For example, a hydroxyl-termination or a carbon structure could be used.

The attachment of a desired bio-molecule to a directly deposited structure allows additional flexibility in the choice of substrates on which the bio-molecules can be immobilized. Additionally, the direct-deposition process allows repeated deposition and attachment to be performed, resulting in a substrate with several different bio-molecules to be attached to a single substrate. Such repeated deposition and attachment avoids repeated lithography steps, which would likely destroy the previously attached bio-molecules.

In some embodiments, the deposition precursor is supplied as a gas precursor, directed towards the substrate surface by a gas injection system within the vacuum chamber of a charged particle beam apparatus. In other embodiments, the deposition precursor is supplied as a liquid. In yet other embodiments, a precursor gas is provided within an enclosure within the vacuum chamber, sometimes known as an environmental cell. If multiple deposition and attachment cycles are performed, the substrate may be removed from the vacuum chamber of the charged particle beam apparatus between subsequent cycles, or any number of the series of cycles may be performed without removal.

Figure 10:
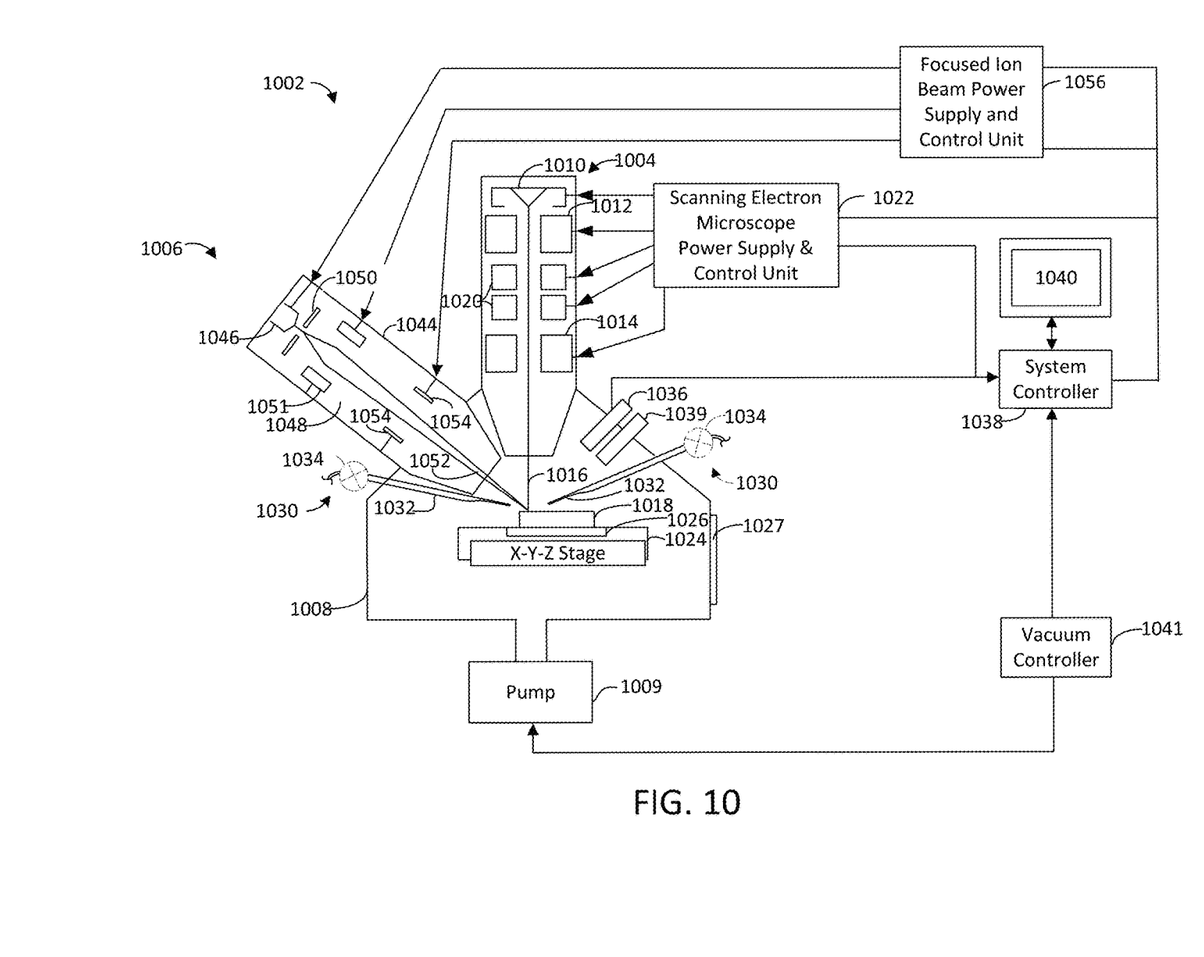
FIG. 10 schematically shows a dual beam system suitable for attaching nano-objects to a substrate.

FIG. 10 depicts an exemplary dual beam system 1002 that can be used to carry out embodiments of the invention. Suitable dual beam systems are commercially available, for example, from FEI Company, Hillsboro, Oreg., the assignee of the present invention. While an example of suitable hardware is provided below, the invention is not limited to being implemented in any particular type of hardware.

Dual beam system 1002 has a vertically mounted electron beam column 1004 and a focused ion beam (FIB) column 1006 mounted at an angle of approximately 52 degrees from the vertical on an evacuable specimen chamber 1008. The specimen chamber may be evacuated by pump system 1009, which typically includes one or more, or a combination of, a turbo-molecular pump, oil diffusion pumps, ion getter pumps, scroll pumps, or other known pumping means.

The electron beam column 1004 includes an electron source 1010, such as a Schottky emitter or a cold field emitter, for producing electrons, and electron-optical lenses 1012 and 1014 forming a finely focused beam of electrons 1016. Electron source 1010 is typically maintained at an electrical potential of between 500 V and 30 kV above the electrical potential of a work piece 1018, which is typically maintained at ground potential.

Thus, electrons impact the work piece 1018 at landing energies of approximately 500 eV to 30 keV. A negative electrical potential can be applied to the work piece to reduce the landing energy of the electrons, which reduces the interaction volume of the electrons with the work piece surface, thereby reducing the size of the nucleation site. Work piece 1018 may comprise, for example, a semiconductor or other material onto which nano-objects are to be attached. The impact point of the beam of electrons 1016 can be positioned on and scanned over the surface of a work piece 1018 by means of deflection coils 1020. Operation of lenses 1012 and 1014 and deflection coils 1020 is controlled by scanning electron microscope power supply and control unit 1022. Lenses and deflection unit may use electric fields, magnetic fields, or a combination thereof.

Work piece 1018 is on movable stage 1024 within specimen chamber 1008. Stage 1024 can preferably move in a horizontal plane (X and Y axes) and vertically (Z axis) and can tilt approximately sixty (60) degrees and rotate about the Z axis. A door 1027 can be opened for inserting work piece 1018 onto X-Y-Z stage 1024 and also for servicing an internal gas supply reservoir (not shown), if one is used. The door is interlocked so that it cannot be opened if specimen chamber 1008 is evacuated. Stage 1024 may be cooled, for example, by a Peltier cooler (not shown) or heated by, for example, a resistive heater 1026.

Mounted on the vacuum chamber are multiple gas injection systems (GIS) 1030 (two shown). Each GIS comprises a reservoir (not shown) for holding the precursor or activation materials and a needle 1032 for directing the gas to the surface of the work piece. Each GIS further comprises means 1034 for regulating the supply of precursor material to the work piece. In this example the regulating means are depicted as an adjustable valve, but the regulating means could also comprise, for example, a regulated heater for heating the precursor material to control its vapor pressure. An optional plasma generator 1039 creates a plasma for exposing the work piece 1018 to a plasma for processing.

When the electrons in the electron beam 1016 strike work piece 1018, secondary electrons, backscattered electrons, and Auger electrons are emitted and can be detected to form an image or to determine information about the work piece. Secondary electrons, for example, are detected by secondary electron detector 1036, such as an Everhard-Thornley detector, or a semiconductor detector device capable of detecting low energy electrons. Signals from the detector 1036 are provided to a system controller 1038 that controls a monitor 1040, which is used to display user controls and an image of the work piece using the signal from detector 1036.

The chamber 1008 is evacuated by pump system 1009 under the control of vacuum controller 1041. The vacuum system provides within chamber 1008 a vacuum of approximately $3 \times 10^{-6}$ mbar. When a suitable precursor or activator gas is introduced onto the sample surface, the chamber background pressure may rise, typically to about $5 \times 10^{-5}$ mbar. The local pressure and gas concentration at the work piece surface are significantly greater than the background pressure and concentration.

Focused ion beam column 1006 comprises an upper neck portion 1044 within which are located an ion source 1046 and a focusing column 1048 including extractor electrode 1050 and an electrostatic optical system including an objective lens 1051. Ion source 1046 may comprise a liquid metal gallium ion source, a plasma ion source, a liquid metal alloy source, or any other type of ion source. The axis of focusing column 1048 is tilted 52 degrees from the axis of the electron column. An ion beam 1052 passes from ion source 1046 through focusing column 1048 and between electrostatic deflectors 1054 toward work piece 1018.

FIB power supply and control unit 1056 provides an electrical potential at ion source 1046. Ion source 1046 is typically maintained at an electrical potential of between 1 kV and 60 kV above the electrical potential of the work piece, which is typically maintained at ground potential. Thus, ions impact the work piece at landing energies of approximately 1 keV to 60 keV. FIB power supply and control unit 1056 is coupled to deflection plates 1054 which can cause the ion beam to trace out a corresponding pattern on the upper surface of work piece 1018. In some systems, the deflection plates are placed before the final lens, as is well known in the art. Beam blanking electrodes (not shown) within ion beam focusing column 1048 cause ion beam 1052 to impact onto blanking aperture (not shown) instead of work piece 1018 when a FIB power supply and control unit 1056 applies a blanking voltage to the blanking electrode.

The ion source 1046 typically provides a beam of singly charged positive gallium ions that can be focused into a sub one-tenth micrometer wide beam at work piece 1018 for modifying the work piece 1018 by ion milling, enhanced etch, material deposition, or for imaging the work piece 1018.

System controller 1038 controls the operations of the various parts of dual beam system 1002. Through system controller 1038, a user can cause ion beam 1052 or electron beam 1016 to be scanned in a desired manner through commands entered into a conventional user interface (not shown). Alternatively, system controller 1038 may control dual beam system 1002 in accordance with programmed instructions. FIG. 10 is a schematic representation, which does not include all the elements of a typical dual beam system and which does not reflect the actual appearance and size of, or the relationship between, all the elements.

A preferred method or apparatus of the present invention has many novel aspects, and because the invention can be embodied in different methods or apparatuses for different purposes, not every aspect need be present in every embodiment. Moreover, many of the aspects of the described embodiments may be separately patentable. The invention has broad applicability and can provide many benefits as described and shown in the examples above. The embodiments will vary greatly depending upon the specific application, and not every embodiment will provide all of the benefits and meet all of the objectives that are achievable by the invention.

In an embodiment, a method of attaching nano-objects to a sample substrate is presented, comprising:

providing a deposition precursor at the surface of the substrate located within the vacuum chamber of a charged particle apparatus;

directing a beam towards the substrate, the beam decomposing the deposition precursor to form a deposit on the surface of the substrate at positions impacted by the beam;

processing the sample to provide linker groups on the surface of the deposit; and processing the sample to chemically bond nano-objects to the linker groups.

In some embodiments, directing a beam towards the substrate comprises directing a charged particle beam towards the surface.

In some embodiments, a charged particle beam image of the surface having attached nano-objects is formed.

In some embodiments, the chemical bond comprises a covalent bond. In some further embodiments, the covalent bond comprises amide, disulfide, sulfonamide, or phosphonamide bonds.

In some embodiments, the nano-objects comprise nano-diamonds or bio-molecules.

In some embodiments, the nano-objects have a critical dimension in the range of between 1 nm and 1000 nm. In some further embodiments, the nano-objects comprise nanodots, crystals, tubes, sheets, or flakes.

In some embodiments, the nano-objects comprise clusters of individual nano-objects. In some further embodiments, the nano-objects comprise clusters of nanodots, crystals, wires, tubes, sheets, or flakes.

In some embodiments, the deposition precursor comprises a carbon-bearing precursor, and the deposit comprises carbon.

In some embodiments, the deposition precursor comprises a sulfur bearing precursor, and the deposit comprises sulfur.

In some embodiments, the deposition precursor comprises a phosphorous bearing precursor, and the deposit comprises phosphorous.

In some embodiments, the deposit has an aspect ratio greater than 1.

In some embodiments, the nano-objects are bonded at the end of the deposit distal from the sample substrate.

In some embodiments, the deposit is sufficiently tall to isolate bonded nano-objects from interaction with the sample substrate.

In some embodiments, the processing the sample to provide linker groups takes place within the vacuum chamber of the charged particle apparatus. In other embodiments, the processing takes places outside of the vacuum chamber.

In some embodiments, the processing the sample to provide linker groups comprises plasma processing. In some further embodiments, the plasma processing comprises processing with an ammonia plasma. In other further embodiments, the plasma processing comprises processing the sample with a liquid. In some embodiments, the liquid is an acid.

In some embodiments, providing linker groups on the surface of the deposit occurs concurrently with the formation of the deposit.

In some embodiments, the processing is performed using a charged particle beam and a precursor gas mixture comprised of a deposition precursor gas and a linker precursor gas. In some embodiments, the linker precursor gas is ammonia. In some embodiments, the charged particle beam is an electron beam, laser beam, or an ion beam.

In some embodiments, the processing the sample to chemically bond nano-objects comprises processing the sample with a liquid containing nano-objects.

In some embodiments, the nano-objects undergo surface processing before bonding to the linker groups. In some embodiments, the surface modification comprises functionalizing the surface of the nano-object with carboxylic acid groups.

Although much of the previous description is directed towards the attachment of nano-diamonds and proteins, the invention could be used to attach nano-scale objects of any suitable material. The terms "work piece," "sample," "substrate," and "specimen" are used interchangeably in this application unless otherwise indicated. Similarly, the terms "deposition," and "deposit" are used interchangeably and refer to the solid material remaining on a surface following a deposition procedure. Further, whenever the terms "automatic," "automated," or similar terms are used herein, those terms will be understood to include manual initiation of the automatic or automated process or step.

In the following discussion and in the claims, the terms "including" and "comprising" are used in an open-ended fashion, and thus should be interpreted to mean "including, but not limited to . . . ." To the extent that any term is not specially defined in this specification, the intent is that the term is to be given its plain and ordinary meaning. The accompanying drawings are intended to aid in understanding the present invention and, unless otherwise indicated, are not drawn to scale.

The various features described herein may be used in any functional combination or sub-combination, and not merely those combinations described in the embodiments herein. As such, this disclosure should be interpreted as providing written description of any such combination or sub-combination.

Although the present invention and its advantages have been described in detail, it should be understood that various changes, substitutions and alterations can be made to the embodiments described herein without departing from the scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of attaching nano-objects to a sample substrate, comprising:
   providing a deposition precursor at the surface of the substrate located within the vacuum chamber of a charged particle beam apparatus;
   directing a beam towards the substrate, the beam decomposing the deposition precursor to form a deposit on the surface of the substrate at positions impacted by the beam;
   processing the sample to provide linker groups on the surface of the deposit by exposing the surface of the sample to a plasma; and
   processing the sample to chemically bond nano-objects to the linker groups.

2. The method of claim 1, wherein directing a beam towards the substrate comprises directing a charged particle beam towards the surface.

3. The method of claim 1, wherein the chemical bond comprises a covalent bond selected from the group consisting of an amide bond, a disulfide bond, a sulfonamide bond, and a phosphonamide bond.

4. The method of claim 1, wherein the nano-objects comprise nanodiamonds or biomolecules.

5. The method of claim 1, wherein the nano-objects comprise a critical dimension in the range of between 1 nm and 1000 nm.

6. The method of claim 5, wherein the nano-objects comprise nano dots, crystals, wires, tubes, sheets or flakes.

7. The method of claim 1, wherein the deposition precursor comprises a carbon-bearing precursor, and the deposit comprises carbon.

8. The method of claim 1, wherein the deposition precursor comprises a sulfur-bearing precursor, and the deposit is substantially sulfur.

9. The method of claim 8, wherein the deposit has an aspect ratio greater than 1.

10. The method of claim 9, wherein the deposit is sufficiently tall to isolate bonded nano-objects from interaction with the sample substrate.

11. The method of claim 1, wherein the deposition precursor comprises a phosphorus-bearing precursor, and the deposit is substantially phosphorus.

12. The method of claim 1, wherein processing the sample to provide linker groups takes place within the vacuum chamber of the charged particle beam apparatus.

13. The method of claim 1, wherein exposing the surface of the sample to a -plasma comprises exposing the surface of the sample to an ammonia plasma.

14. The method of claim 1, wherein the processing is realized by using ammonia vapor as a linker precursor gas.

15. The method of claim 1, in which the beam is a laser beam.

16. The method of claim 1, wherein processing the sample to chemically bond nano-objects comprises processing the sample with a liquid containing nano-objects.

17. The method of claim 1, wherein the nano-objects undergo surface processing before bonding to the linker groups.

18. The method of claim 17, wherein the surface modification comprises functionalizing the surface of the nano-object with carboxylic acid groups.

19. A method of attaching nano-objects to a sample substrate, comprising:
   providing a deposition precursor at the surface of the substrate located within the vacuum chamber of a charged particle beam apparatus;
   directing a beam towards the substrate, the beam decomposing the deposition precursor to form a deposit on the surface of the substrate at positions impacted by the beam;
   processing the sample to provide linker groups on the surface of the deposit; and
   processing the sample to chemically bond nano-objects to the linker groups, wherein the processing is performed using a charged particle beam and a precursor gas mixture comprised of a deposition precursor gas and a linker precursor gas.

20. The method of claim 19 in which:
   providing a deposition precursor at the surface of the substrate located within the vacuum chamber of a charged particle beam apparatus includes providing a carbon precursor; and
   directing a beam towards the substrate, the beam decomposing the deposition precursor to form a deposit on the surface of the substrate at positions impacted by the beam includes forming a carbon deposit on the surface at positions impacted by the beam.

* * * * *